(12) United States Patent
Cervenka et al.

(10) Patent No.: US 8,163,965 B2
(45) Date of Patent: Apr. 24, 2012

(54) CONTINUOUS CRYSTALLISATION PROCESS OF IODINATED PHENYL DERIVATIVES

(75) Inventors: Jan Cervenka, Oslo (NO); Khalid Hussain, Oslo (NO); Arne W. Aabye, Oslo (NO)

(73) Assignee: GE Healthcare AS, Olso (NO)

( * ) Notice: Subject to any disclaimer, the term of this patent is extended or adjusted under 35 U.S.C. 154(b) by 0 days.

(21) Appl. No.: 11/996,982

(22) PCT Filed: Jul. 28, 2006

(86) PCT No.: PCT/NO2006/000289
§ 371 (c)(1),
(2), (4) Date: Jan. 28, 2008

(87) PCT Pub. No.: WO2007/013816
PCT Pub. Date: Feb. 1, 2007

(65) Prior Publication Data
US 2008/0194876 A1    Aug. 14, 2008

(30) Foreign Application Priority Data

Jul. 29, 2005    (NO) .................................... 20053676

(51) Int. Cl.
| | |
|---|---|
| *C07C 22/00* | (2006.01) |
| *C07C 25/00* | (2006.01) |
| *C07C 17/38* | (2006.01) |
| *C07C 233/00* | (2006.01) |
| *C07C 235/00* | (2006.01) |
| *C07C 237/00* | (2006.01) |
| *C07C 239/00* | (2006.01) |

(52) U.S. Cl. .......................... 570/211; 570/190; 564/153
(58) Field of Classification Search ........................ None
See application file for complete search history.

(56) References Cited

U.S. PATENT DOCUMENTS

| | | | |
|---|---|---|---|
| 6,469,208 B1 * | 10/2002 | Villax et al. .................. | 564/153 |
| 6,646,171 B2 * | 11/2003 | Cervenka ...................... | 570/177 |
| 2008/0214867 A1 * | 9/2008 | Cervenka et al. ............. | 564/153 |

FOREIGN PATENT DOCUMENTS

| | | |
|---|---|---|
| EP | 0747344 | 12/1996 |
| WO | 2005/003080 | 1/2005 |
| WO | 2006/016815 | 2/2006 |

OTHER PUBLICATIONS

Paul, E. et al. Powder Technology 150 (2005) 133-143.*
U.S. Appl. No. 11/573,283, filed Feb. 2007, Cervenka, Jan.*
PCT/NO2006/000289 Int'l Search Report/Written Opinion dated Nov. 2006.

* cited by examiner

*Primary Examiner* — Daniel Sullivan
*Assistant Examiner* — Clinton Brooks

(57) ABSTRACT

The invention describes a process for the purification of iodinated aryl compounds where the purification is performed by continuous crystallization of a crude product in a solvent with removal of at least a fraction of the solvent. The continuous crystallization process is performed in one or more crystallizers at the boiling point of the content of the crystallizer.

14 Claims, No Drawings

CONTINUOUS CRYSTALLISATION PROCESS OF IODINATED PHENYL DERIVATIVES

This application is a filing under 35 U.S.C. 371 of international application number PCT/NO2006/000289, filed Jul. 28, 2006, which claims priority to application number 20053676 filed Jul. 29, 2005, in Norway the entire disclosure of which is hereby incorporated by reference.

TECHNICAL FIELD OF INVENTION

The invention relates to a process for the purification by crystallisation of iodinated aryl compounds such as iodinated X-ray contrast agents which allows for purification in an efficient and safe manner at a low cost. The invention relates in particular to industrial scale processes.

DESCRIPTION OF RELATED ART

A vast number of iodinated aryl compounds are known from the state of art. Of these, triiodinated phenyl derivatives are commonly used as X-ray contrast agents. Triiodinated phenyl compounds, containing three iodine atoms in meta positions to one another in the phenyl ring and various substituents at one or more of the non-iodine substituted phenyl carbons, are frequently achieved in multiple conformations with steric hindrance to transitions between such conformations. The so-called dimeric compounds, which contain two iodophenyl groups linked via a linking group such as an optionally substituted alkylene bridging group, are particularly constrained by the bulky substituents.

In the final step of the primary production process, the crude product containing the iodinated aryl compounds such as iodophenyl compounds has to be purified. A common system for purification is purification by crystallisation. To promote the crystal growth kinetics, the crystallisation needs to take place at elevated temperature. The crystallisation is also promoted by high supersaturation. However, high supersaturation may result in limited purity of the crystallised compounds. The crystallisation process is very demanding in terms of time and equipment size and will take several days to perform. The crystallisation step is often a bottleneck in industrial scale processes.

The crystallisation is performed as batch processes. The batch size in industrial scale is usually from several hundred kilos and up to several tons and demands crystallisation equipment of considerable size. Many attempts have therefore been made to accelerate the process.

EP 747 344 A1 discloses purification and crystallisation of iopamidol by refluxing the solution at atmospheric pressure. WO 99/18054 discloses a batch process for the crystallisation of e.g. triiodophenyl group containing compounds by effecting the crystallisation under elevated pressure.

Various solvent systems are proposed to provide proper saturation or supersaturation of the product in the solvent when using batch crystallisation processes, see e.g. U.S. Pat. No. 4,250,113, EP 747 344, GB 2 280 436, WO 98/08804, WO 99/18054, WO 02/083623 and WO 2005/003080.

In addition to searching for processes that are easier to perform and less demanding with regards to time consumption and need for costly equipment, the main challenge in the production process is to meet the criteria for purity as set by the Health Authorities for X-ray contrast agents to be suitable for in vivo administration e.g. for intravenous administration. For example, the European Pharmacopea specifies the purity for the dimeric compound iodixanol (1,3-bis(acetamino)-N,N'-bis[3,5bis-(2,3-dihydroxypropylaminocarbonyl)-2,4,6-triiodophenyl]-2-hydroxypropane) which is the active pharmaceutical ingredient (API) of the commercial X-ray contrast agent Visipaque™ and for the monomeric compound iohexyl (5-(acetyl(2,3-dihydroxypropyl)amino)N,N'-bis(2,3-dihydroxypropyl)-2,4,6-triiodobenzene-1,3-dicarboxamide)) which is the active pharmaceutical ingredient (API) of the commercial X-ray contrast agent Omnipaque™ of not less than 98.0%.

It has now surprisingly been found that iodinated aryl compounds such as iodophenyl compounds can successfully be purified by a continuous crystallisation process.

SUMMARY OF THE INVENTION

In one embodiment the present application provides a process for the purification of iodinated aryl compounds by continuous crystallisation of the corresponding crude product containing the compounds in a solvent by removing at least a fraction of the solvent during the process. Specifically, iodophenyl compounds such as those used as active pharmaceutical ingredients (API) in X-ray contrast agents for in vivo use can be produced by a continuous crystallisation process. By performing the crystallisation as a continuous process the yield per volume and time unit of the equipment is increased while the purity level of the crystallised iodinated compounds are maintained and may even be increased.

DETAILED DESCRIPTION OF THE INVENTION

In its broadest scope the invention relates to a process for the purification of iodinated aryl compounds where the purification is performed by continuous crystallisation of the compound from a crude product in a solvent by removing at least a fraction of the solvent during the process.

By the removal of at least a fraction of the solvent a state of saturation or supersaturation of the compound in the solvent is achieved. This will facilitate the crystallisation of the desired purified compound from the solvent.

The supersaturation of the compound can be further enhanced by the addition of an anti-solvent or a mixture of anti-solvents to the solution of the compound in the solvent during the continuous crystallisation process.

By solvent is meant a liquid or a mixture of liquids wherein the compound is generally well soluble whereas by anti-solvent is meant a liquid or a mixture of liquids wherein the compound is less soluble and preferably significantly less soluble than in the solvent.

Various anti-solvents for the use in the crystallisation of iodinated aryl compounds are known from the prior art as discussed above. In the purification process of the invention, a mixture of anti-solvents can beneficially be employed in the process. Use of mixtures of anti-solvents will enable the generation of anti-solvents that have the desired properties with regard to solubility of the compound to be crystallised and the boiling point of the anti-solvent.

Alternatively, selection of one single anti-solvent for the use in the crystallisation process is also possible. Use of a single anti-solvent is usually preferred when this anti-solvent can fulfil the criteria mentioned for mixtures of anti-solvents.

The term anti-solvent in the further specification comprises a mixture of anti-solvents or a single anti-solvent and the term solvent comprises a single solvent or a mixture of solvents. In general, singular and plural forms are used interchangeable in this document.

In the present invention the solvent may be removed by any procedure known from the state of art. However, it is preferred to remove the solvent by distilling off the solvent during the continuous crystallisation process. Thin film evaporation techniques are also preferred. The solvents will be removed so that an optimal supersaturation is achieved during the process so as to obtain a crystalline compound that is substantially free of impurities. It is further preferred that the crystals are easily filterable and that they are obtained in good yield.

The use of anti-solvents that forms an azeotrope with the solvent wherein the crude product to be crystallised is dissolved may be beneficial. Preferably the azeotrope should contain a high percentage of the solvent to be removed during the crystallisation process.

Iodinated aryl compounds and in particular iodinated phenyl compounds (collectively denoted compound/compounds) for use as API in in vivo X-ray contrast agents are soluble in water and the X-ray contrast agents are usually provided commercially as aqueous solutions of the API. This class of compounds are usually sterically hindered organic compounds and a high input of thermal energy is needed for the compounds to adopt a conformation required by the crystalline structure. Hence, the thermal energy needed is provided by working at elevated temperatures up to the boiling point of the content of the crystallisers. The boiling point of the anti-solvents and the anti-solvents in mixture with the solution of the crude product to be crystallised should therefore be moderate, and at a temperature where the iodinated compound and other constituents of the crude product and the solvents are stable. Preferably the boiling point of solvents and anti-solvents should be below 150° C. at ambient pressure, more preferably below 120° C., e.g. from 30° C. to 110° C. The crystallisation should be effected at a temperature below 200° C., preferably below 150° C. and particularly below 120° C. The crystallisation should be effected at ambient pressure or at elevated pressure e.g. at an overpressure of from 0.05 to 20 bar. The crystallisation should is performed at the boiling point of the solution, i.e. the content of the actual crystalliser at the specific pressure used in the crystallisation process and preferably at ambient pressure.

The anti-solvent should be fully mixable with the solution of the crude product. When the anti-solvent is added to the crude product in solution, a saturation or supersaturation of the crude product is created and the compound will crystallise from the boiling solution.

The anti-solvents for the compound to be crystallised from the crude product is usually selected from alcohols, ketones, esters, ethers and hydrocarbons, especially alcohols, alcohol-ethers, ethers and ketones, e.g. $C_{2-5}$ alcohols. Examples of suitable anti-solvents include ethanol, n-propanol, isopropanol, n-butanol, i-butanol, sec-butanol, t-butanol, pentanols including isoamyl alcohol, acetone, ethyl-methyl ketone, formaldehyde, acetaldehyde, dimethyl ether, diethyl ether, methylethyl ether, tetrahydrofuran, ethylacetate, acetonitrile, dimethylsulphoxide, dimethylformamide, dimethylacetamide, benzene, toluene, xylene, n-hexane, cyclohexane, n-heptane, etc. and mixtures of these compounds. Especially preferred are $C_1$-$C_5$-monoalkylether of a $C_2$-$C_{10}$ alkylene glycol such as 1-metoxy-2-propanol, and a 2-propanol.

The crude product is obtained from the primary production of the compounds. The primary production is a multistep synthetic procedure wherein the aryl group, e.g. the phenyl group, is substituted by hydroxy-alkyl and/or acylamino and/or alkylaminocarbonyl groups that are optionally further substituted by hydroxy groups, amino groups, ether groups and similar groups or the alkyl chains may contain oxo or thio groups. The aryl groups are further substituted by iodine atoms, for phenyl groups usually by three iodo atoms in meta positions to one another. Tri-iodinated phenyl compounds as well as dimers and multimers of such compounds and in particular non-ionic compounds thereof are as noted above useful as API of X-ray contrast media.

Examples of such momomers and dimers are diatrizoate, iobenzamate, iocarmate, iocetamate, iodamide, iodipamide, iodixanol, iohexyl, iopentol, ioversol, iopamidol, iotrolan, iodoxamate, ioglicate, ioglycamate, iomeprol, iopanoate, iophenylate, iopromide, iopronate, ioserate, iosimide, iotasul, iothalamate, iotroxate, ioxaglate, ioxitalamate, metrizamide, metrizoate, iobitritol, ioxaglic acid, iosimenol and other compounds from the state of art including monomers and dimers known from WO96/09285 and WO96/09282.

Several of the monomers and dimers listed above are the API of commercial X-ray contrast agents for example iohexyl of Omnipaque™, iopamidol of Isovue™, iomeprol of Iomeron™, iopromide of Ultravist™, iotrolan of Isovist™, iodixanol of Visipaque™ and iotribitrol of Xenetix™. These products are produced in high quantities and efficient and economic viable processes are continuously sought.

The products mentioned above and their manufacturing processes are known from the literature and from patent publications, e.g. from U.S. Pat. No. 4,364,921, U.S. Pat. No. 4,250,113, U.S. Pat. No. 5,349,085, U.S. Pat. No. 4,001,323, U.S. Pat. No. 4,352,788, U.S. Pat. No. 4,341,756 and U.S. Pat. No. 5,043,152.

Prior to the crystallisation, the solution containing the crude product from the primary production can be further purified. Preferably, if the solution of the crude product contains amounts of salt, the solution can be fully or partially desalinated e.g. by treatment on ion exchange columns. Any solvents used during the chemical synthetic steps should also be reduced if necessary to an amount not interfering substantially with the crystallisation process. The solvents and the prospective azeotropes of the solvents should have a boiling point lower than the temperature where the compound starts to disintegrate, but high enough so that sufficient energy can be supplied to promote the crystallisation process.

The solution may also be concentrated by the removal of parts of the solvent e.g. under vacuum and/or by azeotropic distillation. For example, the amount of water as solvent can vary from 5% to 100% by weight of the crude product, preferably below 50% by weight.

The crude product from the synthesis optionally pretreated as explained above is used as the feeding stream to the crystalliser. The crystallisation unit comprises one or more crystallisation tanks, at least one of which is equipped with a distillation column and at least one inlet for the feeding stream and one outlet for the product stream. The tank should further be equipped with a heater, e.g. as a jacket for temperature control and may also be equipped with a mixing device. Optionally the tank comprises further inlet and outlet openings e.g. for feeding of additional anti-solvents and/or for extracting samples. The feeding and the extraction is preferably performed by pumping liquid in and out, however other arrangements are also feasible like utilising the gravity force.

The crystallisation unit may further be equipped to enable pressurising the content of the crystalliser.

The crystalliser where the feeding of the crude product in solution is performed, is preferably preloaded with a suitable amount of crystals of the product to be crystallised suspended in the solvent, e.g. water, and in one or more of the anti-solvents. The use of seed crystals will enhance the initial crystallisation process and promote the establishment of steady state conditions.

When commencing the crystallisation process the feeding stream comprising the solution of the crude product preferably pretreated as described above, is loaded into a crystalliser preferably equipped as described above and preloaded with a suspension of crystals. The removal of the solvent, preferably by distillation, controls the generation of the supersaturation of the compound in the solvent. If an anti-solvent is used, and in particular when the solvent and the anti-solvent form an azeotrope that is distilled off, anti-solvent is fed to the crystalliser either through the same inlet or through a separate inlet.

Preferably the crude product in solution and the anti-solvent when used are fed into the crystalliser at constant rates. The crystallised compound of the product stream is withdrawn at constant rate as a suspension. The sum of the feeding rate of the crude product in solution (F1) equals the amount of solvent which is distilled off (F2) and the amount of compound withdrawn as the product stream (F3), in other words, F1=F2+F3 at steady state. If an anti-solvent is used in an amount of F4, the steady state is characterised in that F1+F4=F2+F3. The feeding rates and the removal of solvent and also of anti-solvent when the solvent and the anti-solvent form an azeotrope will decide the resident time of the compound in the crystalliser. The residence time may be set according to the kinetic of the crystallising compound and the required production capacity. The optimal residence time in each crystalliser is dependent on the number and volume of crystallisers employed and will be optimised for each specific process.

The feeding rates F1 and optionally F4 may be the same or different depending on the concentration of the compound and anti-solvent in the feeding streams.

A process is considered to be at steady state if the process variables do not change with time. The steady state is characterised by a particular solvent and anti-solvent content, temperature, mother liquor concentration, magma density and particle size distribution.

The crystallisation process is run using one or more crystallisers. Each crystalliser is preferably equipped with a distillation column. The crystallisers will usually be coupled in series, optionally with partial recycling of the product stream and mother liquor or crystals after filtration from a crystalliser to one or more previous crystalliser in the series as will be explained in more detail below. The overall solubility decreases from the first to subsequent crystalliser by the removal of the solvent and optionally by the addition of a balanced amount of anti-solvent to the crystallisers when used.

Although sufficient yield and purity of the compound can be achieved in one crystalliser only, it is generally preferable to run the process in two or more crystallisers. Hence, by using multiple crystallisers the total yield of the compounds is divided and the process is performed more gently. This may be beneficial for the total yield, filterability as well as the purity of the crystallised compound.

There are several combinations of flow pattern that can be employed in the continuous crystallisation process, e.g. by employing the required number of crystallisers in series, by recycling the whole or part of the recovered material from the final crystalliser or from an intermediate crystalliser to a previous crystalliser or a combination of such procedures.

For example, a continuous crystallisation can be performed by setting up two or more crystallisers, e.g. three crystallisers, in series. One or more of the crystallisers are equipped with distillation columns for the removal of the solvent, optionally as an azeotropic mixture. The first crystalliser, which is preferably preloaded with crystals, is loaded with the crude product in solution and optionally with an anti-solvent. The temperature in the crystalliser is adjusted to the boiling point of the content and solvent (in mixture with anti-solvent when azeotropic distillation is performed) is distilled off. The suspension (product stream) from the first crystalliser is transferred to a second crystalliser and kept boiling. The solvent content is further reduced by the removal of the solvent by distillation. When the solvent content is reduced, more compound is crystallised. Optionally, an additional amount of anti-solvent or solvent/anti-solvent is added to keep the required volume of the content of the crystalliser. The suspension (product stream) can be transferred to further crystallisers in the series and treated as described in the second crystalliser until sufficient material is crystallised. As a final step, the suspension may be transferred to a crystalliser where the temperature is below the boiling point of the content of the crystalliser. In this unit, which does not need to be equipped with a distillation column, the driving force is reduction in solubility by cooling. The final crystalline compound is isolated from the last crystalliser by filtration and washing (if needed) and can also be dried and collected as a dry crystalline compound.

In this arrangement the concentration of crystals will be high in all crystallisers and the solvents are quickly removed from the process. The required residence time is short and the size of the crystallisers can be relatively small. However, this arrangement is sensitive to the deposition of impurities in the compound since the final crystalline compound is isolated from the impurity enriched mother liquor. This arrangement will therefore be most suited when the level of impurities is relatively low and/or the purification selectivity by crystallisation is high.

An alternative arrangement comprises to arrange for recycling of the recovered material and to withdraw the compound in the form of a product stream from a crystalliser that is not the final crystalliser in the series.

This arrangement comprises a number of crystallisers, for example three crystallisers arranged as explained above. The stream from the first crystalliser is withdrawn and fed into the second and further crystallisers. All crystallisers are optionally equipped with distillation towers and heated so to maintain the content at the boiling point. The stream of a suspension of crystals or the filtered crystals from a crystalliser is recirculated to one of the previous crystallisers, for example to the first crystalliser either directly or after dissolution in the feeding stream of the crude product in the solvent. The crystalline compound is withdrawn from this crystalliser, filtered and washed and dried if desired. This arrangement has the benefit that the purity of the final crystalline compound is very good and the yield may be further enhanced. On the other hand, the magma density of the $2^{nd}$ and further crystallisers is reduced and this may require prolonged residence times and a larger volumes of the crystallisers. The noted disadvantages can however be reduced by recycling an amount of the crystals from the last tank to the first crystalliser and to one or more of the intermediate crystallisers.

In further alternatives the process can be run as a combination of a continuous crystallisation process and a batch crystallisation process where the compound is mainly crystallised in the continuous crystallisation process before the remaining crystallisation is performed as a batch crystallisation process. It is also possible to perform the initial crystallisation in a batch crystallisation fashion and then to continue the crystallisation as a continuous crystallisation process, preferably in the same crystalliser. The purpose of this arrangement is to achieve a sufficient amount of crystals in the solution before switching over to the continuous crystallisation mode. The continuous crystallisation process may be followed by a batch crystalliser from which the compound is withdrawn and if necessary or desirable is washed and dried before the compound is collected.

In a preferred embodiment the invention comprises a process for continuous crystallisation of iohexyl and iodixanol from water and potentially further solvents, using 1-metoxy-2-propanol as anti-solvent and using single or multiple crystallisers equipped with distillation columns. The process is run at normal boiling temperature of the content of the crystallisers or higher temperatures when using elevated pressure.

A feed stream containing about 0.1-0.7 l water per kg of the crude iohexyl or crude iodixanol product and from 1 to 4 l of 1-metoxy-2-propanol per kg of crude iohexyl or 1-4 l of 1-metoxy-2-propanol per kg of crude iodixanol product, is added continuously to the crystalliser containing a suspension of the crystals at a rate of F1 (amount of crude product and solvents/anti-solvents per time unit). The crystalliser is continuously heated. The water/1-metoxy-2-propanol azeotrope is continuously distilled off from the distillation tower at a rate of F2 (amount of azeotrope per time unit). The water content is by this reduced to the desire level, normally up to 0.1 l per kg crude iohexyl product and 0.15-0.25 l per kg crude iodixanol product. The suspension of crystalline compound in solvent (product stream), is continuously transferred to the second crystalliser in the cascade at a rate F3 (amount per time unit) that keeps the volume in the crystalliser constant or to the filter unit. Hence, F1=F2+F3 at steady state. The volume may also be adjusted by addition, e.g. continuous addition, at a rate of F4, of 1-metoxy-2-propanol during the crystallisation process.

The overall solubility will decrease from the first crystalliser to the final crystalliser in the cascade. To achieve a satisfactory result with regards to purity, crystal size and yield, the continuous crystallisation may be performed in more than one crystalliser to achieve optimal supersaturation in each crystalliser.

Pure 1-metoxy-2-propanol has a boiling point of 119° C. and forms an azeotrope with water boiling at 97.5° C. This azetrope contains about 49% of water. At the boiling point of 97.5° C. iohexyl and iodixanol is supplied with sufficient thermal energy to crystallise relatively quickly from the solution.

The invention will now be further described by the non-limiting examples. All % are weight % if not specified otherwise.

Example 1

Continuous Crystallisation of Iohexyl from Water/1-methoxy-2-propanol

A crude product solution was made by dissolving the crude product containing 96.7% iohexyl in a mixture of 0.2 ml water/g crude product and 1.0 ml 1-methoxy-2-propanol/g crude product.

Iohexyl was crystallised from solution of crude product in 1-methoxy-2-propanol and water. Supersaturation was generated by continuous azeotropic water removal. The crystallisation was performed in a stirred jacketed steel crystalliser of 1100 ml working volume. The crystalliser was equipped with distillation tower for water removal and pumps for control of the inlet flows (the crude product solution and the 1-methoxy-2-propanol) and outlet flows (the distillate and product suspension). The inlet flows were equipped with heat exchangers for pre-heating the crude product solution and 1-methoxy-2-propanol.

The continuous crystallisation process was initiated in the crystalliser preloaded with 300 g iohexyl crystals in 1000 ml boiling 1-methoxy-2-propanol under full reflux. The pre-heated crude product solution and 1-methoxy-2-propanol were continuously fed into the crystalliser containing the boiling suspension at a rate of 8.8 ml/min and 21.1. ml/min, respectively. Water was continuously removed as a 1-methoxy-2-propanol/water distillate at a rate of 6.6 ml/min. Suspension of the crystals was continuously withdrawn from the crystalliser keeping the suspension volume in the crystalliser constant. A steady state was achieved after about 3 hours operation. The residence time of the suspension in the crystalliser was 47 minutes. At steady state the concentration of the UV-absorbing substance (at 245 nm) in the mother liquor was 5.9%. The water content in the mother liquor at steady state was 1.05%. Purity of the crystalline iohexyl product was 99.0%.

The throughput per crystalliser volume and time unit of the continuous crystallisation process was 315 kg iohexyl/m$^3$ hour. In the corresponding batch process a typical throughput is 12 kg iohexyl/m$^3$ hour.

Example 2

Continuous Crystallisation of Iodixanol from Water/1-methoxy-2-propanol

A crude product solution was made by dissolving 2605 g of the crude product containing 91.9% iodixanol in a mixture of 1250 ml water and 3000 ml of 1-methoxy-2-propanol.

Iodixanol was crystallised from a solution of crude product in 1-methoxy-2-propanol and water. Supersaturation was generated by continuous azeotropic water removal. The crystallisation was performed in a stirred jacketed steel crystalliser of 1100 ml working volume. The crystalliser was equipped with distillation tower for water removal and pumps for control of the inlet flows (crude product solution and 1-methoxy-2-propanol) and outlet flows (distillate and product suspension).

The continuous crystallisation process was initiated in the crystalliser preloaded with 355 g of iodixanol crystals suspended in a mixture of 800 ml 1-methoxy-2-propanol, 30 ml water and 100 ml stock solution of the crude product. After the crystalliser was brought to boiling and total reflux through the distillation tower established, all the pumps were started and kept going in 46 hours. The flows were chosen to keep the residence time of 7.5 hours:

| | |
|---|---|
| 1-methoxy-2-propanol | 1.61 ml/min |
| Crude product solution | 1.27 ml/min |
| Distillate | 0.44 ml/min |

Concentration of water in the distillate was 41.6%.

At steady state, the concentration of the UV-absorbing substance (at 244.5 nm) in the mother liquor was 4.4%. The water content in the mother liquor at steady state was 6.0%. The total amount of solvents was 3.5 l per kg of dry crude product (0.2 l/kg of water and 3.3 l/kg of 1-methoxy-2-propanol). Purity of the crystalline iodixanol product after filtration and washing with methanol was 98.7%.

The throughput per crystalliser volume and time of the continuous crystallisation process was 34 kg iodixanol/m$^3$ h. In the corresponding batch process a typical throughput is 5.6 kg iodixanol/m$^3$ h.

What is claimed is:

1. A continuous process for the purification of iohexyl or iodixanol by crystallization comprising the following steps:

i) feeding crude product and solvent into a crystallizer;
ii) removing at least a fraction of the solvent to achieve and maintain supersaturation; and
iii) establishing steady state conditions wherein:
   (a) crude product in solution is continuously fed into the crystallizer at constant rate;
   (b) crystallized compound in suspension is continuously withdrawn at constant rate;
   (c) solvent is withdrawn at a constant rate, and
   (d) the volume load of the crystallizer is kept constant.

2. Process of claim 1 wherein the solvent is removed by distillation.

3. Process of claim 1 wherein an anti-solvent, in which the compound is less soluble than in the solvent, is added.

4. Process of claim 1 wherein the continuous crystallisation process is performed in one or more crystalliser at the boiling point of the content of the unit.

5. Process of claim 1 wherein the process is performed at the boiling point at ambient pressure.

6. Process of claim 1 wherein the process is performed at the boiling point at elevated pressure.

7. Process of claim 1 wherein the solvent and the anti-solvent is removed by azeotropic distillation.

8. Process of claim 1 wherein the process is performed using one or more crystallisation units.

9. Process of claim 3 wherein the feeding rate of the crude product in solution and of the anti-solvent if present are decided by the resident time of the compound in the crystallisers.

10. Process of claim 1 wherein the process further comprises a batch crystallisation step.

11. Process of claim 3 wherein the anti-solvent comprises solvents of the group comprising alcohols, ketones, esters, ethers and hydrocarbons.

12. Process of claim 11 wherein the anti-solvent comprises $C_1$-$C_5$-monoalkylether of a $C_2$-$C_{10}$ alkylene glycol.

13. Process of claim 12 wherein the anti-solvent comprises 1-methoxy-2-propanol.

14. Process of claim 1 wherein the solvent comprises water.

* * * * *